United States Patent [19]

Aldrich et al.

[11] Patent Number: 5,447,718

[45] Date of Patent: Sep. 5, 1995

[54] PHEROMONE COMPOSITIONS FOR ATTRACTING *EUSCHISTUS SPP.* INSECTS

[75] Inventors: Jeffrey R. Aldrich, College Park, Md.; Michael P. Hoffmann, Davis, Calif.; Jan P. Kochansky; William R. Lusby, both of Adelphi, Md.; Lloyd T. Wilson, Woodland; Frank G. Zalom, Davis, both of Calif.

[73] Assignees: The United States of America as represented by the Secretary of Agriculture, Washington, D.C.; The Regents of the University of California, Oakland, Calif.

[21] Appl. No.: 461,890

[22] Filed: Jan. 8, 1990

[51] Int. Cl.⁶ ............................................. A01N 25/00
[52] U.S. Cl. ................................................. 424/84
[58] Field of Search ................................... 424/84

[56] References Cited

U.S. PATENT DOCUMENTS 3,541,203  11/1970  Fogle et al. .......................... 424/17
3,866,349   2/1975  Meijer et al. ......................... 43/114

OTHER PUBLICATIONS

Lofqvist et al CA 107: 193069p 1987.
Panizzi, et al., Florida Entomol., vol. 68, No. 1, (1985), pp. 184–214.
Aldrich, J. R., "Chemistry and Biological Activity of Pentatomoid Sex Pheromones," Biologically Active Natural Products: Potential Use in Agriculture, ACS Symposium Series No. 380, Cutler, H. G., (ed.), 1988, pp. 417–431.
Aldrich, J. R., Ann. Rev. Entomol, vol. 33, (1988), pp. 211–238.
Byers, et al., Naturwissenschaften, vol. 75, (1988), pp. 153–155.
Baeckstrom, et al., Tetrahedron, vol. 44, No. 9, 1988), pp. 2541–2548.
Hoffmann, et al., (Calif. Agric., vol. 41, (1987), pp. 4–6.
Warner, "Conjugated Fatty Acids from Latex of Euphorbia Lathyris", Phytochemistry, vol. 20, pp. 89–91, 1981.

*Primary Examiner*—Marianne M. Cintins
*Assistant Examiner*—Russell Travers
*Attorney, Agent, or Firm*—M. Howard Silverstein; Randall E. Deck; John D. Fado

[57] ABSTRACT

Compositions and methods are provided for attracting and subsequently trapping and/or killing crop pests from the Euschistus species. Alkyl esters of (2E,4Z)-decadienoic acid as a chemical attractant pheromone and, in combination with a trap or toxicant, provide an efficient means for controlling these insects.

11 Claims, 3 Drawing Sheets methyl (2E,4E)-decadienoate methyl (2Z,4E)-decadienoate (E)-geranylacetone decanoic acid

PHEROMONE COMPOSITIONS FOR ATTRACTING *EUSCHISTUS SPP.* INSECTS

BACKGROUND OF THE INVENTION

1. Field of the Invention

This invention relates to compositions and methods for attracting, trapping and/or killing crop pests from Euschistus species known as stink bugs.

1. Description of the Prior Art

The genus Euschistus is the largest of the genera in the so-called stink bug family Pentatomidae (order Hemiptera: suborder Heteroptera). Over 60 Euschistus species have been described, including 18 from North America. Several Euschistus species are among the most common members of the family in the western hemisphere and, to many people, these large brown insects are recognized as the stink bug.

Euschistus adults are strong fliers and often migrate to a succession of maturing crops where they feed on developing fruits or seeds. The immature bugs usually disperse from the initial point of attack, thereby spreading the infestation. As with other kinds of stink bugs, Euschistus adults and immatures suck sap or oil through hypodermic-like mouthparts, thus inconspicuously damaging the most valuable portion of the crop. Their feeding also indirectly reduces yield and seed quality by transmitting diseases. In the absence of food or with the onset of winter, adults are able to hibernate and resume attack the following season.

Various Euschistus species attack a wide range of fruit, field crops, vegetables, and nut crops. In the western United States the consperse stink bug, *E. conspersus*, is a major pest of tomatoes and also causes "catfacing" of apples, peaches, pears, grapes, and other fruits. During years of high *E. conspersus* populations, cotton and seed alfalfa yields in California have been seriously reduced. East of the Rocky Mountains three other Euschistus species are serious agricultural pests of field, vegetable, fruit, and nut crops: *E. servus*, the brown stink bug; *E. variolarius*, the onespotted stink bug; and *E. tristigmus*, the dusky stink bug. One or more of these Euschistus species frequently coexist with the green stink bugs, *Acrosternum hilare* and *Nezara viridula*, to form a complex that, along with the corn earworm, is the most damaging of the soybean pod feeders in the southern U.S. Although stink bug damage to soybean is less severe in more northerly regions of the U.S., the widespread use of reduced tillage crop systems has vastly increased the threat of *E. servus* and *E. viriolarius* to corn. This threat has arisen in fields under a soybean/corn or wheat/corn rotation because the brown and onespotted stink bugs overwinter in soybean and wheat stubble, then feed on emerging corn seedlings in the spring. A single stink bug can cause irrevocable damage to a corn plant in less than 24 hours. In Central and South America other species of Euschistus bugs are important pests. For example, *E. heros* is one of the three major stink bug pests of soybean in Brazil.

Outbreaks of Euschistus and other stink bugs are difficult to control because the bugs can migrate into a field and irreversibly damage a crop before they are noticed. Population build-ups that go undetected my lead to infestations of later maturing crops or outbreaks the following season. Moreover, several stink bug species usually coexist at varying abundances from region to region and year to year, further complicating monitoring and control strategies.

Although the use of insecticides has increased the quality and quantity of crop yields, there are serious disadvantages to the use of presently available insecticides. The toxicity to humans and animals is high. Additionally, they are not readily degraded and may thus pollute the environment. Therefore, reducing or eliminating the amount of toxic insecticides used in the management of insect pests is desirable. It is an object of the present invention to provide compositions and methods by which the amounts of pesticide may be reduced or eliminated in eradicating Euschistus species stink bugs.

Attractant pheromones have recently been identified for several species of predatory and plant-feeding stink bugs. F. Warnaar [Phytochemistry, Vol. 20, (1981), pp. 89–91] disclosed the mass spectra (MS) of methyl (2E,4Z)-decadienoate and methyl (2E,4E)-decadienoate, both of which closely resemble the MS of the *E. conspersus* male-specific compound.

Additionally, there has been reported a strong synergism between methyl E,Z-2,4-decadienoate and chalcogran at attracting the bark beetle, Pityogenes chalcographus [Byers, et al., Naturwissenschaften, Vol. 75, (1988), pp. 153–155]. The reference does not indicate a utility for the attraction and/or management of insects of the Euschistus species.

SUMMARY OF THE INVENTION

A chemical attractant pheromone for Euschistus species as well as methods for concentrating and destroying these pests is provided. In one alternative embodiment the attractant could be used to monitor area levels of these pests. In another embodiment the attractant would be useful for concentrating these pests in early maturing "trap-crops" where they could be economically destroyed by limited insecticide application. Analogously, this chemical attractant could be applied to artificially create overwintering aggregations of adults that would then be destroyed, thus preventing spring outbreaks.

DETAILED DESCRIPTION OF THE INVENTION

EXAMPLE 1

Isolation of Pheromones.

*Euschistus conspersus* adults were collected near Davis, California and reared in the laboratory at the UC-Davis Entomology Department on sunflower seeds, green beans, and water. Volatiles were trapped from groups of 10–30 virgin adult males or females by coaxing the bugs into a ca. 1 liter glass column and drawing air by vacuum (100 ml/min) over the bugs through 30 mg of activated charcoal for 24 hr. Trapped volatiles were washed from the filter in 200–300 $\mu l$ of $CH_2Cl_2$ and stored under nitrogen at $-20°$ C.

In four months, four species of Euschistus stink bugs were caught in traps deployed at the Agricultural Research Center, Beltsville, Md.: *E. servus*, *E. tristigmus*,

*E. variolarius*, and *E. politus*. Field-collected adults and/or laboratory-reared adults of *E. servus*, *E. tristigmus*, and *E. politus* were used for aeration experiments as for *E. conspersus*. In addition, specimens of *E. obscurus* and *E. ictericus* were obtained from Florida and aerated for pheromone isolation.

Figure 1:
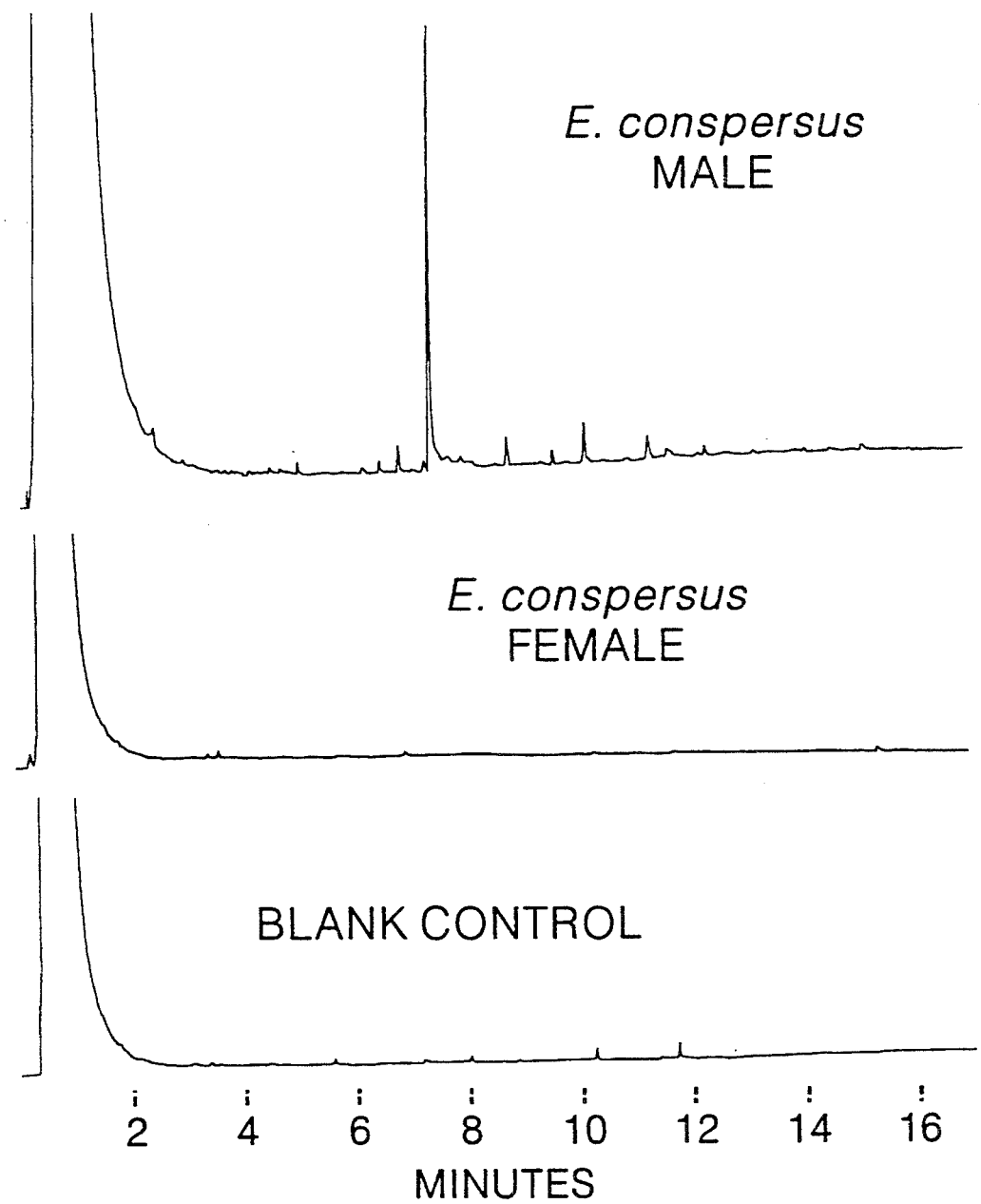
FIG. 1 shows the peak and elution time of the attractant pheromone obtained from aeration experiments.

Samples were analyzed by gas chromatography (GC) on a bonded methyl silicone column (0.25 μm film, 14-mm ID; DB-1 TM, J&W Scientific, Folsom, Calif.) using a Varian 3700 GC with helium as carrier (40 cm/sec), and a temperature program from 45° C. for 2 min to 230° C. at 15°/min. When the odor of the stink gland secretion was detected at the start of a male or female aeration, or when one or mere adults died during the aeration, usually only the stink gland secretion components were detected by GC. However, in uncontaminated aeration samples of mature male Euschistus species a single major component eluting at 7.4 min was observed (FIG. 1). This component was never present in samples from female Euschistus species. Other minor components (<5%) were detected in some male Euschistus samples.

EXAMPLE 2

Identification of Pheromone Components.

Figure 2:
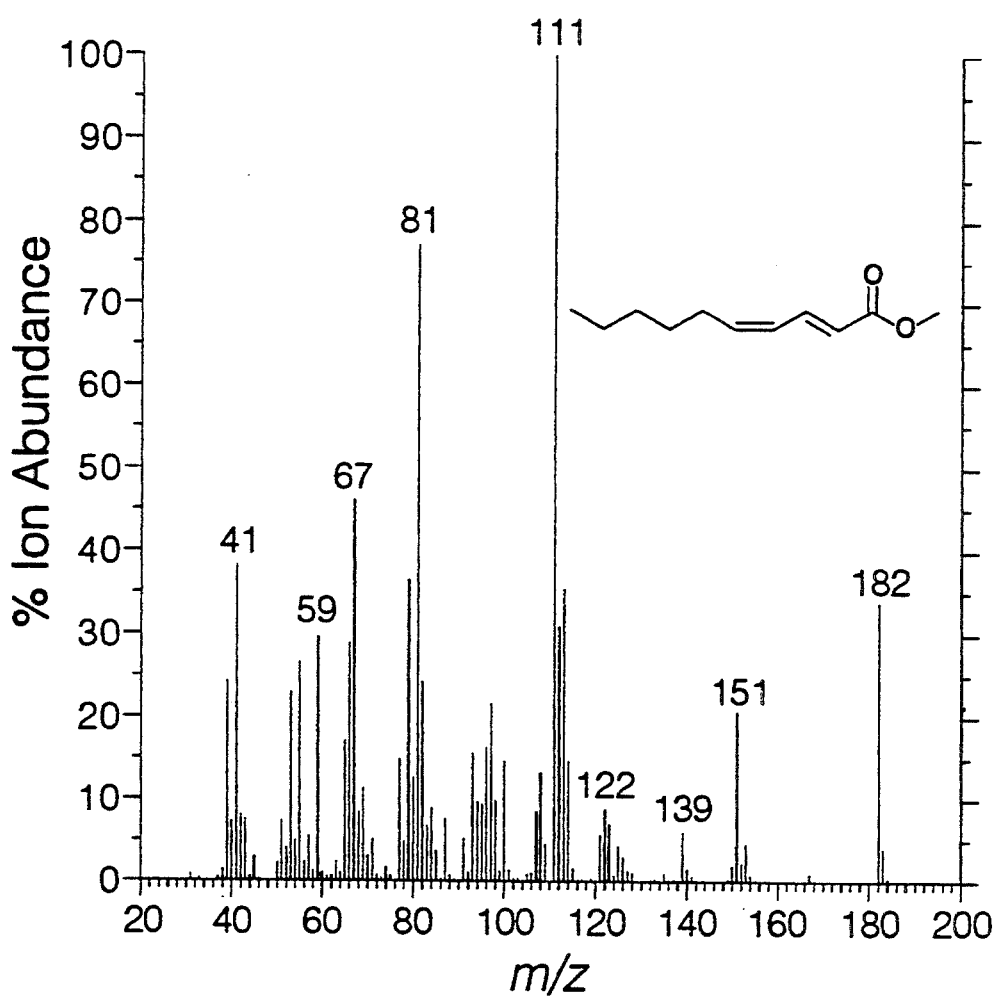
FIG. 2 is the mass spectrum and chemical structure of methyl (2E,4Z)-decadienoate.

Mass spectra (MS) were obtained in the electron impact mode at 70 eV using a Finnigan 4510 GC-MS. The MS of the major male-specific compound detected in *E. conspersus* aeration samples gave a prominent molecular ion a m/z 182 (ca. 20%), but a matching spectrum was not found in the GC-MS computer library of spectra (>31,000 MS) (FIG. 2). The presence of an M-31 peak at m/z 151 suggested a methyl ester structure for this component, as did ions at m/z 59 ($[O=C-O-CH_3]^+$) and m/z 74 ($[CH_2=C(OH)-OCH_3]^+$). Thus, the molecular formula was deduced to be $C_{11}H_{18}O_2$ and a di-unsaturated, unbranched acidic moiety was thought most likely. A 20 g sample of the related compound, ethyl (2E,4Z)-decadienoate (called the pear ester), was obtained from International Flavors & Fragrances Inc. (IFF, Union Beach, N.J.). The pear ester standard was saponified and re-esterified with methanol by normal procedures to give methyl (2E,4Z)-decadienoate and a small percentage of the corresponding (2Z,4E)- and (2E,4E)-isomers. This standard of methyl (2E,4Z)-decadienoate gave an identical MS to that of the *E. conspersus* male-specific compound and the standard coeluted with the unknown by GC.

Figure 3:
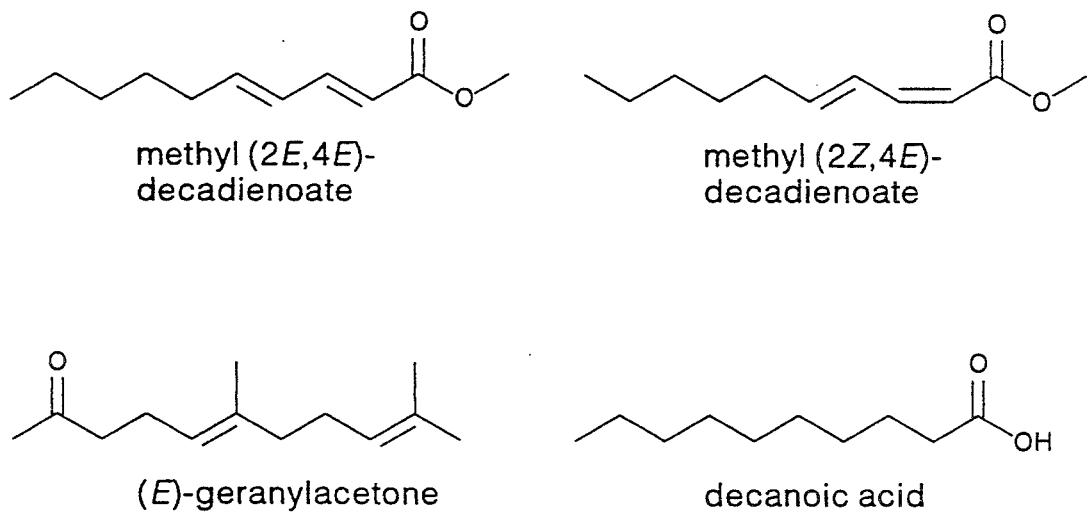
FIG. 3 shows the structure of some minor male-specific volatile components from Euschistus spp.

Certain minor components were identified from Euschistus male aeration samples (FIG. 3). Methyl (2E,4E)-decadienoate (2–7%) was present in extracts from all species examined except *E. tristigmus*. Methyl (2Z,4E)-decadienoate (0.2%) was also detected in an extract of *E. politus*. Decanoic acid (ca. 10%) was detected in a sample from *E. tristigmus* males. Geranyl acetone (6,10-dimethyl-5E,9-undecadien-2-one) (ca. 5%) occurred in extracts from *E. conspersus*, *E. servus*, and *E. tristigmus*.

EXAMPLE 3

Behavioral Testing.

Two field tests for *E. conspersus* attraction were conducted in Yolo County, California, in the following manner. Traps consisted of one gallon transparent plastic cylindrical containers with wire mesh funnels inserted in opposite sides of the container. A rubber septum (Thomas Scientific) was used as a receptacle for the pheromone. Each septum was washed with $CH_2Cl_2$, clipped inside a piece of PVC pipe (2.5 cm diameter×3.0 cm length), and suspended 7.0 cm from the top of the trap. Traps were baited by applying either 1 μl or 10 μl of methyl (2E,4Z)-decadienoate in the septum, followed by 100 μl of $CH_2Cl_2$; control traps lacked the ester. The first field tests used material prepared from the pear ester obtained from IFF Inc. as described above consisting of 88% methyl (2E,4Z)-decadienoate, 9% of the corresponding (2Z,4E)-isomer, and 3% of the (2E,4E)-isomer. The second field tests used material purchased from Bedoukian Research Inc. (Danbury, Conn.) determined by GC and GC-MS to contain 92.1% methyl (2E,4Z)-decadienoate, 1.4% of the (2Z,4E)-isomer, and 6.5% of the (2E,4E)-isomer. Traps were placed on the ground ca. 20 m apart in a randomized block design, checked and rotated daily, and rebaited at 3–5 day intervals.

Field tests for the attraction of Euschistus species native to the eastern U.S. were conducted at the Beltsville Agricultural Research Center, Prince George's County, Md., as follows. Transparent plastic traps were constructed as for the California field tests except that the rubber septum was fastened in the bottom of the trap and was unprotected by PVC pipe. One test also used traps constructed of 15×25 cm transparent plastic sheets coated on each side with Tack Trap TM. A rubber septum was fastened in a 4 cm diameter hole in the center of the sheet. The bottom and sides of the trap had a 1.5 cm perpendicular rim that prevented insects from falling off the trap. Traps were hung from tree branches at least 20 m apart along powerline clearings through forest and around the borders of grassland, or from stakes at least 10 m apart in a weedy field. The following lures were tested: 1) methyl (2E,4Z)-decadienoate (Bedoukian Research Inc.), 2) ethyl (2E,4Z)-decadienoate (IFF Inc.), 3) 60% methyl (2E,4Z)-decadienoate/40% decanoic acid (Aldrich Chemical), and 4) 98.5% methyl (2E,4Z)-decadienoate/1.5% geranylacetone (Bedoukian Research Inc.). One part of each of these lures was blended with 2 parts of heptane. Traps were monitored daily and rebaited at 2–3 day intervals with 10 μl of a solution; control traps were unbaited.

*Euschistus conspersus* females and males were significantly attracted to the 10 μl dosage of methyl (2E,4Z)-decadienoate in the California field tests (Tables 1 and 2). Small nymphs of *E. conspersus* were also significantly attracted to this ester, and many more medium- and large-sized nymphs were caught in baited traps than control traps but not at a significant level because of high variability between traps (Table 2).

In a later field test conducted in and around forest at the Agricultural Research Center, Beltsville, Md., 201 *E. tristigmus*, 67 *E. politus*, 8 *E. servus*, and 76 tachinid fly parasites of Euschistus bugs were attracted to traps baited with methyl (2E,4Z)-decadienoate; whereas, only one female *E. tristigmus* and five tachinids were attracted to unbaited controls (Tables 3 and 4). *Euschistus tristigmus* adults and tachinid parasites were significantly more attracted to methyl (2E,4Z)-decadienoate than ethyl (2E,4Z)-decadienoate ($Chi^2$=9.81 and 22.62, respectively; Table 3). The inclusion of decanoic acid with methyl (2E,4Z)-decadienoate did not significantly improve attraction of any Euschistus species or parasites (Table 4). Similarly, inclusion of geranyl acetone with methyl (2E,4Z)-decadienoate did not improve attraction (Table 5), although small samples may have precluded detection of this effect.

There has been provided in accordance with the present invention, compositions and methods for controlling insects of the Euschistus species that do not suffer the disadvantages described by the prior art. It can be seen from the specification and specific embodiments therein that there are many alternatives and variations apparent to those skilled in the art. It is understood that all such alternatives and variations are included within the spirit and scope of the invention.

TABLE 1

Chemical Attraction of *Euschistus conspersus*, Yolo County, CA.

| | Number Trapped | | | | | | | |
|---|---|---|---|---|---|---|---|---|
| | Test I* | | | | Test II** | | | |
| Treatment | nymph | male | female | total † | nymph | male | female | total † |
| blank | 0 | 0 | 0 | 0a | 0 | 0 | 1 | 1a |
| 1 μl methyl 2E,4Z-decadienoate | 1 | 5 | 6 | 12b | 3 | 0 | 1 | 4a |
| 10 μl methyl 2E,4Z-decadienoate | 0 | 5 | 2 | 7b | 2 | 6 | 14 | 22b |

*Test I: 4 replications per treatment in weedy dwarf peach orchard.
**Test II: 5 replications per treatment in sugar beet field.
† Data subjected to ANOVA after log (x + 1) transformation. Total means in a column not followed by a common letter are significantly different at the 5% level by Duncan's Multiple Range Test.

TABLE 2

Chemical attraction of *Euschistus conspersus*;, Yolo County.*

| | Mean Catch/Trap** | | | | | |
|---|---|---|---|---|---|---|
| | Nymphs † | | | Adults | | |
| Treatment | small | medium | large | male | female | Total |
| blank | 2.6a | 2.4a | 1.6a | 0.8a | 0.4a | 7.8a |
| 10 μl methyl 2E,4Z-decadienoate | 16.8b | 10.4a | 11.4a | 7.8b | 9.0b | 55.4b |

*Five replications per treatment in a weedy field or blackberry patch.
**Data subjected to ANOVA after log (x + 1) transformation. Means in a column not followed by a common letter are significantly different at the 5% level by Duncan's Multiple Range Test.
† Small nymphs = 2nd instars, medium nymphs = 3-4th instars, large nymphs = 4-5th instars.

TABLE 3

Chemical attraction of Euschistus species and parasitic tachinids, Prince George's County, Maryland.*

| | Treatment [No. Attracted]** | | |
|---|---|---|---|
| Insect | methyl 2E,4Z)-decadienoate | ethyl 2E,4Z-decadienoate | Blank |
| *E. tristigmus* | | | |
| male | 50 | 24 | 0 |
| female | 22 | 15 | 1 |
| *E. politus* | | | |
| male | 17 | 13 | 0 |
| female | 30 | 18 | 0 |
| *E. servus* | | | |
| male | 0 | 0 | 0 |
| female | 3 | 0 | 0 |
| Tachinid Parasites † | 60 | 18 | 5 |

*Six sticky-trap replications and 6 transparent cylindrical-trap replications per treatment deployed in and around deciduous forest.
**Number attracted includes insects within 1 m of a trap.
† The following tachinid species were captured: *Gymnosoma par, Euthera tentatrix, Gymoclytia occidua,* and *Euclytia flava*.

TABLE 4

Chemical attraction of Euschistus species and parasitic tachinids, Prince George's County, Maryland.*

| | Treatment [No. Attracted]** | | |
|---|---|---|---|
| Insect | methyl 2E,4Z-decadienoate | methyl 2E,4Z-decadienoate + decanoic acid | Blank |
| *E. tristigmus* | | | |
| male | 54 | 52 | 0 |
| female | 71 | 74 | 0 |
| nymph | 4 | 13 | 0 |
| *E. politus* | | | |
| male | 6 | 10 | 0 |
| female | 9 | 15 | 0 |
| nymph | 5 | 3 | 0 |
| *E. servus* | | | |
| male | 1 | 5 | 0 |
| female | 2 | 4 | 0 |
| nymph | 1 | 2 | 0 |
| Tachinid Parasites † | 16 | 10 | 0 |

*Six transparent cylindrical-trap replications per treatment deployed in same location as test of Table 3.
**Number attracted includes within 1 m of a trap.
† The following tachinid species were captured: *Gymnosoma par, Euthera tentatrix,* and *Euclytia flava*.

TABLE 5

Chemical attraction of Euschistus species and parasitic tachinids, Prince George's County, Maryland.*

| | Treatment [No. Attracted]** | |
|---|---|---|
| Insect | methyl 2E,4Z-decadienoate | methyl 2E,4Z-decadienoate + geranylacetone |
| *E. servus* | | |
| male | 9 | 6 |
| female | 4 | 6 |
| *E. variolarius* | | |
| male | 1 | 0 |
| female | 0 | 0 |
| *E. servus/variolarius* nymphs † | 0 | 3 |
| Tachinid Parasites † † | 12 | 9 |

*Three replicates per treatment deployed in weedy field.
**Number attracted includes insects within 1 m of a trap.
† Nymphs of *E. servos* and *E. variolarius* could not be distinguished.
† † The following tachinid species were captured: *Gymnosoma fuliginosum, Euthera tentatrix,* and *Gymnoclytia occidua*.

We claim:

1. A pesticide composition for killing Euschistus species crop pests comprising:
   a) an alkyl ester of (2E,4Z)-decadienoic acid, and
   b) an effective amount of a toxicant sufficient for killing insects of the genus Euschistus, and wherein said composition does not include chalcogran.

2. The pesticide composition of claim 1, wherein the alkyl ester is a methyl ester.

3. The pesticide composition of claim 1, wherein the alkyl ester is an ethyl ester.

4. The pesticide composition of claim 1, wherein the toxicant is a biocontrol agent.

5. The pesticide composition of claim 1, wherein the toxicant is a pesticide.

6. A pesticide composition for killing Euschistus species crop pests comprising:

a) a chemical attractant consisting essentially of an alkyl ester of (2E,4Z)-decadienoic acid, and b) an effective amount of a toxicant sufficient for killing insects of the genus Euschistus.

7. The pesticide composition of claim 6, wherein the alkyl ester is a methyl ester.

8. The pesticide composition of claim 6, wherein the alkyl ester is an ethyl ester.

9. The pesticide composition of claim 6, wherein the toxicant is a biocontrol agent.

10. The pesticide composition of claim 6, wherein the toxicant is a pesticide.

11. The pesticide composition of claim 6, wherein said chemical attractant consists of an alkyl ester of (2E,4Z)-decadienoic acid.

* * * * *